US012797033B2

(12) United States Patent
Chung

(10) Patent No.: US 12,797,033 B2
(45) Date of Patent: Nov. 17, 2026

(54) BLOOD FLOW MEASUREMENT SYSTEM

(71) Applicant: EDGECARE INC., Seoul (KR)

(72) Inventor: Mann Sik Chung, Seoul (KR)

(73) Assignee: EDGECARE INC., Seoul (KR)

( * ) Notice: Subject to any disclaimer, the term of this patent is extended or adjusted under 35 U.S.C. 154(b) by 37 days.

(21) Appl. No.: 18/861,675

(22) PCT Filed: Jan. 16, 2023

(86) PCT No.: PCT/KR2023/000743
§ 371 (c)(1),
(2) Date: Oct. 30, 2024

(87) PCT Pub. No.: WO2024/005294
PCT Pub. Date: Jan. 4, 2024

(65) Prior Publication Data

US 2026/0182950 A1 Jul. 2, 2026

(30) Foreign Application Priority Data

Jul. 1, 2022 (KR) ........................ 10-2022-0081347

(51) Int. Cl.
*A61B 8/00* (2006.01)
*A61B 8/06* (2006.01)
*A61B 8/12* (2006.01)

(52) U.S. Cl.
CPC .................. *A61B 8/06* (2013.01); *A61B 8/12* (2013.01); *A61B 8/488* (2013.01); *A61B 8/54* (2013.01)

(58) Field of Classification Search
CPC ........................................................ A61B 8/06
See application file for complete search history.

(56) References Cited

U.S. PATENT DOCUMENTS

2010/0210946 A1* 8/2010 Harada ................ A61B 8/4281 600/443
2020/0008686 A1* 1/2020 Khair ..................... A61B 5/029
2021/0113194 A1* 4/2021 Padwal ................ A61B 8/4477

FOREIGN PATENT DOCUMENTS

KR 10-2010-0080533 7/2010
KR 10-2013-0139704 12/2013
KR 10-2015-0027482 3/2015
KR 10-2019-0044758 5/2019
KR 10-2447518 9/2022

* cited by examiner

*Primary Examiner* — Joseph M Santos Rodriguez
(74) *Attorney, Agent, or Firm* — LEX IP MEISTER, PLLC

(57) ABSTRACT

A blood flow measurement system, according to an embodiment of the present disclosure, may comprise: a first blood flow measuring device; and a second blood flow measuring device. The first blood flow measuring device may include: a first image guide probe; and a 1-1 Doppler probe and a 1-2 Doppler probe disposed in a direction perpendicular to the first image guide probe. The second blood flow measuring device may include: a second image guide probe; and a 2-1 Doppler probe and a 2-2 Doppler probe disposed in a direction perpendicular to the second image guide probe. The blood flow measurement system, according to the present disclosure, can more effectively monitor a patient's condition by measuring blood flow information at a plurality of points by using the plurality of blood flow measuring devices each including the image guide probe and the plurality of Doppler probes disposed in the direction perpendicular to the image guide probe.

10 Claims, 4 Drawing Sheets

10

[FIG. 1]
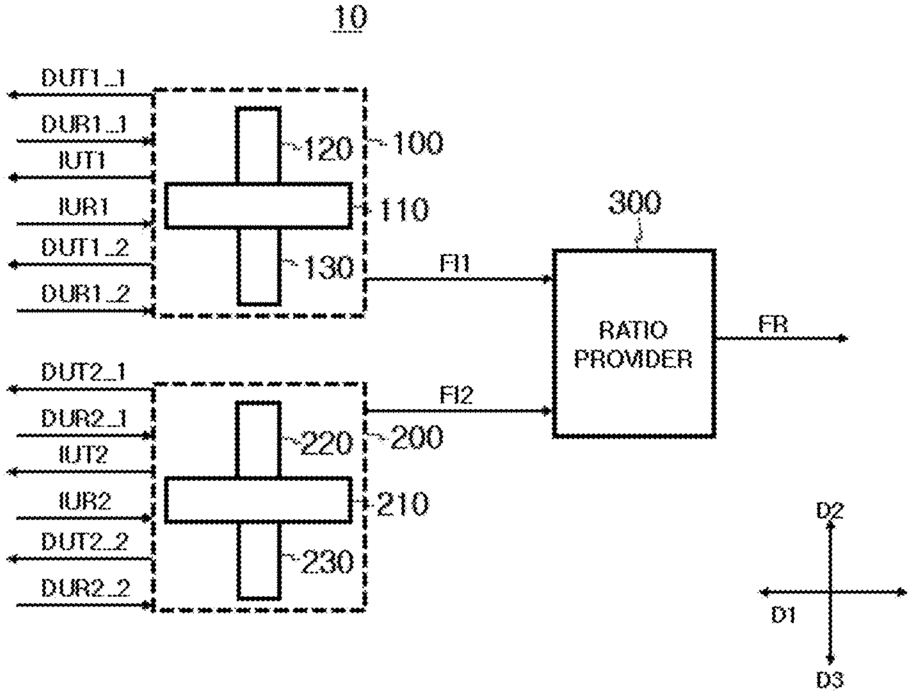
[FIG. 2]
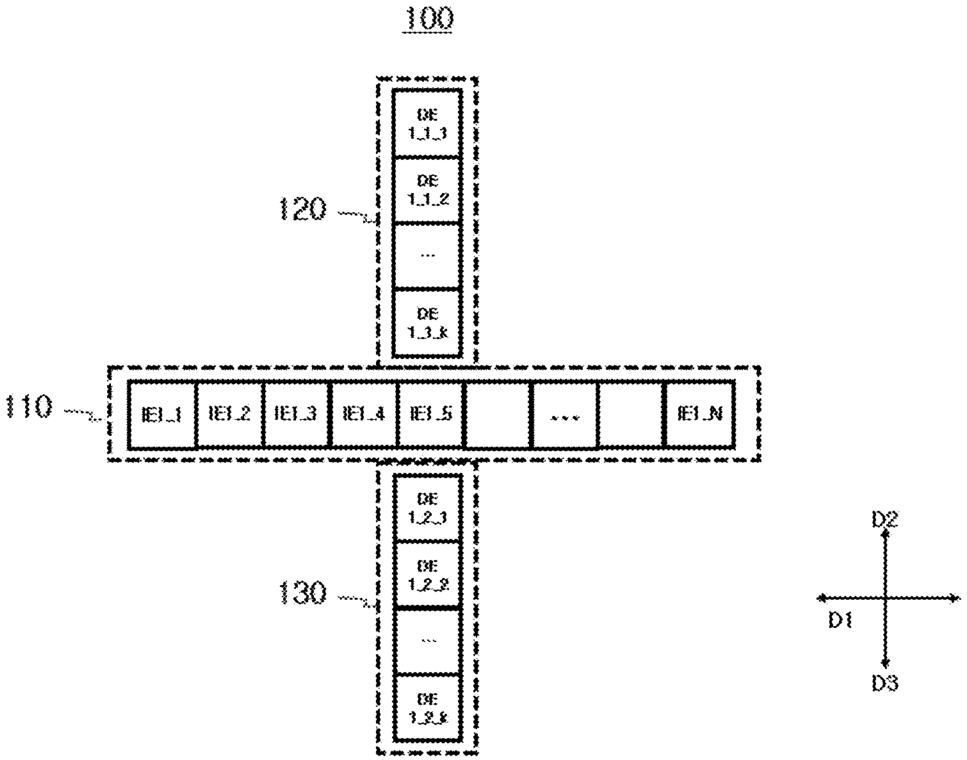

[FIG. 3]
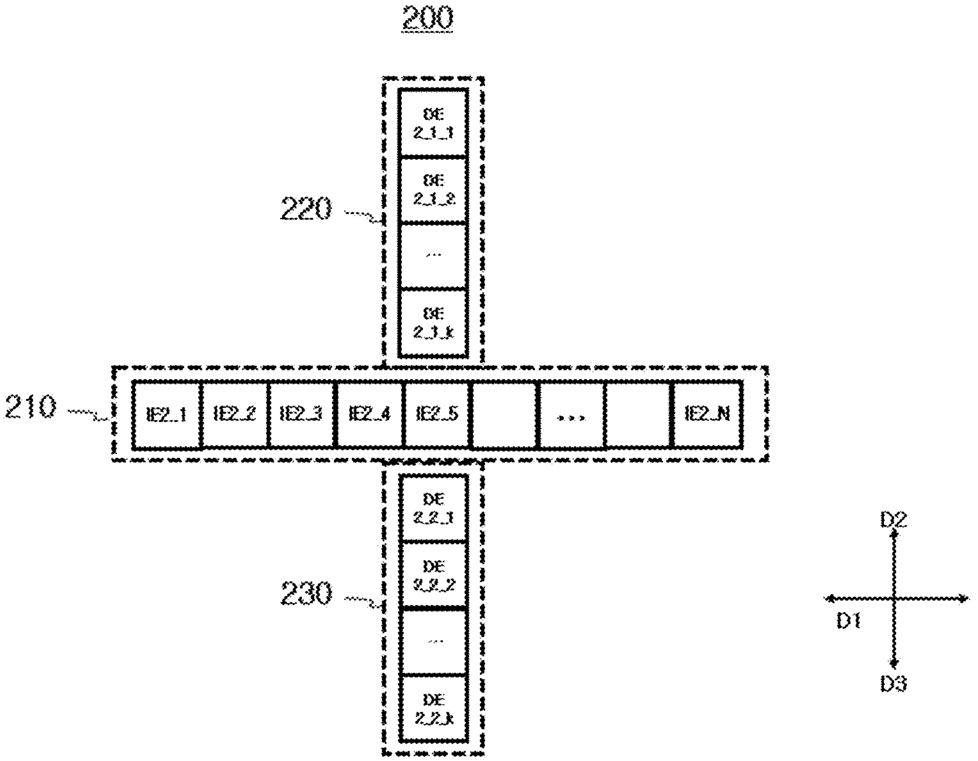
[FIG. 4]
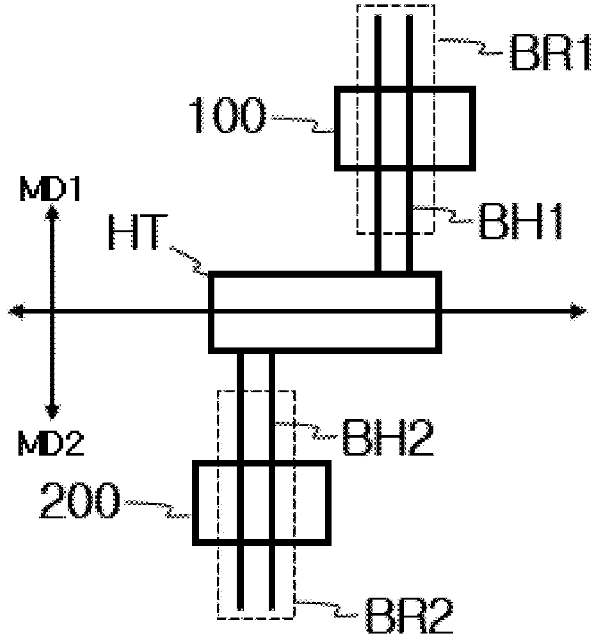

[FIG. 5]
| FIRST BLOOD FLOW INFORMATION (FI1) | SECOND BLOOD FLOW INFORMATION (FI2) | BLOOD FLOW RATIO (FR) |
|---|---|---|
| 3 | 7 | 3:7 |
[FIG. 6]
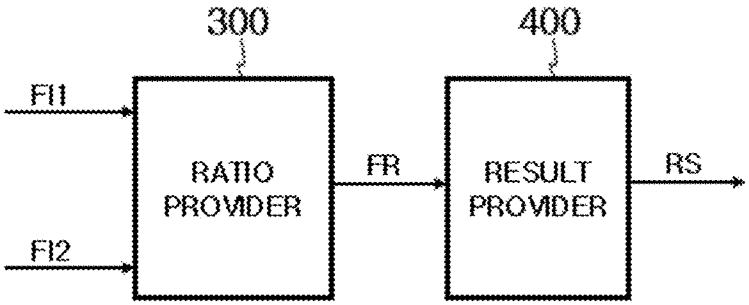
[FIG. 7]
OPERATION MODE (MD)
| | DETAILS OF OPERATION |
|---|---|
| FIRST OPERATION MODE | IMAGE GUIDE |
| SECOND OPERATION MODE | DOPPLER MEASUREMENT |
[FIG. 8]
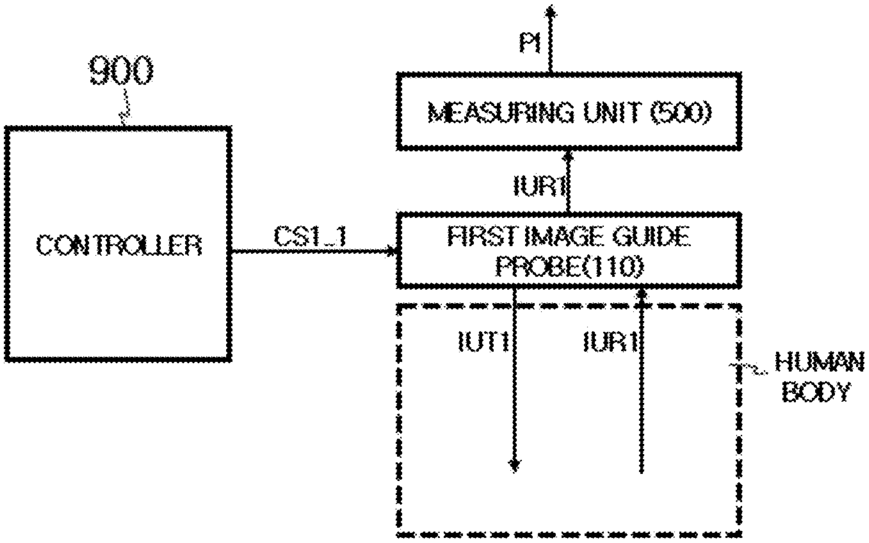

[FIG. 9]
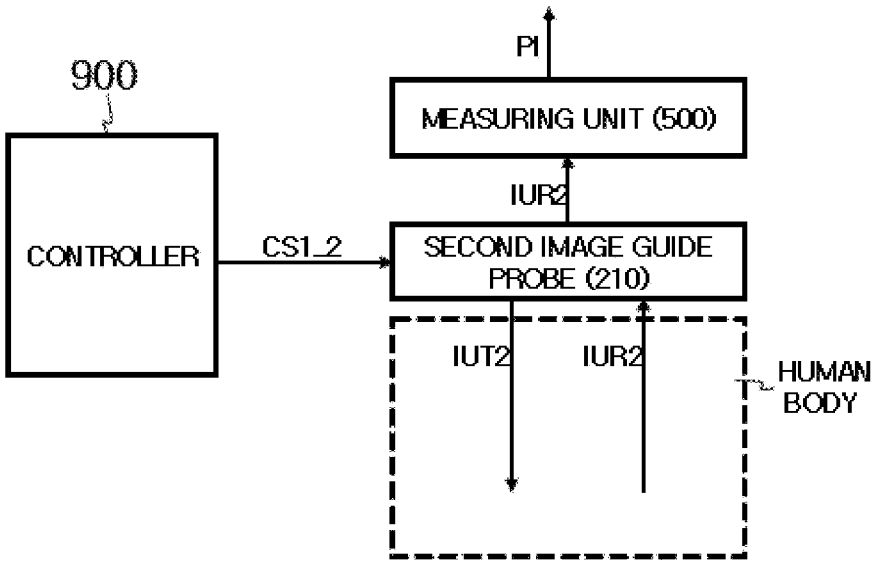

BLOOD FLOW MEASUREMENT SYSTEM

TECHNICAL FIELD

The present disclosure relates to a blood flow measurement system.

BACKGROUND ART

Recently, studies for monitoring the conditions of patients by securing blood flow information in various ways are being conducted with the development of the system for measuring blood flow.

DISCLOSURE

Technical Problem

An object of the present disclosure provides a blood flow measurement system that can effectively monitor the condition of a patent by measuring blood flow information at a plurality of points using a plurality of blood flow measuring devices including an image guide probe and a plurality of Doppler probes disposed in a direction perpendicular to the image guide probe.

Technical Solution

In one general aspect, a blood flow measurement system according to an embodiment of the present disclosure may include a first blood flow measuring device and a second blood flow measuring device. The first blood flow measuring device may include a first image guide probe, and a 1_1 Doppler probe and a 1_2 Doppler probe that are disposed in a direction perpendicular to the first image guide probe. The second blood flow measuring device may include a second image guide probe, and a 2_1 Doppler probe and a 2_2 Doppler probe that are disposed in a direction perpendicular to the second image guide probe.

The first blood flow measuring device may be disposed in a first blood vessel region corresponding to a blood vessel disposed in a first measurement direction with respect to the heart in a human body, and the second blood flow measuring device may be disposed in a second blood vessel region corresponding to a blood vessel disposed in a second measurement direction corresponding to the opposite direction of the first measurement direction with respect to the heart.

The blood flow measurement system may further include a ratio provider. The ratio provider may provide a blood flow ratio corresponding to a ratio between a value of first blood flow information measured from the first blood flow measuring device and a value of second blood flow information measured from the second blood flow measuring device.

The blood flow measurement system may further include a result provider. The result provider may provide a warning signal when the blood flow ratio departs from a predetermined reference range.

The first blood flow information and the second blood flow information may include a velocity time interval (VTI), a stroke volume (SV), and cardiac output.

The first blood flow measuring device may include a first guide image probe, a 1_1 Doppler probe, and a 1_2 Doppler probe. The first guide image probe may include a plurality of first image ultrasonic elements and may be disposed in a first direction. The 1_1 Doppler probe may include a plurality of 1_1 Doppler ultrasonic elements and may be disposed at a side of the first guide image probe in a second direction corresponding to a direction perpendicular to the first direction. The 1_2 Doppler probe may include a plurality of 1_2 Doppler ultrasonic elements and may be disposed at another side of the first guide image probe in a third direction corresponding to a direction perpendicular to the first direction.

The second blood flow measuring device may include a second guide image probe, a 2_1 Doppler probe, and a 2_2 Doppler probe. The second guide image probe may include a plurality of second image ultrasonic elements and may be disposed in the first direction. The 2_1 Doppler probe may include a plurality of 2_1 Doppler ultrasonic elements and may be disposed at a side of the second guide image probe in the second direction corresponding to a direction perpendicular to the first direction. The 2_2 Doppler probe may include a plurality of 2_2 Doppler ultrasonic elements and may be disposed at another side of the second guide image probe in the third direction corresponding to a direction perpendicular to the first direction.

The blood flow measurement system may further include a controller. The controller may provide control signals for controlling the first blood flow measuring device and the second blood flow measuring device. The blood flow measurement system may include a plurality of operation modes, and, in a first operation mode of the plurality of operation modes, the controller drives the first guide image probe and the second guide image probe on the basis of a first control signal of the control signals, and a measuring unit may measure position information of a blood vessel on the basis of a first image ultrasonic reception signal and a second image ultrasonic reception signal that are received to the first guide image probe and the second guide image probe.

In a second operation mode of the plurality of operation modes after the first operation mode, the controller may alternately drive the 1_1 Doppler probe and the 1_2 Doppler probe at every driving interval corresponding to a preset predetermined time interval.

A 1_1 Doppler ultrasonic reception signal reflecting from a blood vessel of the human body that is obtained from the 1_1 Doppler ultrasonic transmission signal provided from the 1_1 Doppler probe may be received to the 1_2 Doppler probe.

Other than the objects of the present disclosure stated above, other features and advantages of the present disclosure may be described below, or the present disclosure would be clearly understood by those skilled in the art from the description.

Advantageous Effects

According to the present disclosure, there are the following effects.

The blood flow measurement system according to the present disclosure can more effectively monitor the condition of a patent by measuring blood flow information at a plurality of points using a plurality of blood flow measuring devices including an image guide probe and a plurality of Doppler probes disposed in a direction perpendicular to the image guide probe.

Further, other features and advantages of the present disclosure may be newly found through embodiments of the present disclosure.

BRIEF DESCRIPTION OF THE DRAWINGS

FIG. 1 is a diagram showing a blood flow measurement system according to embodiments of the present disclosure.

FIG. 2 is a diagram showing a first blood flow measuring device included in the blood flow measurement system of FIG. 1.

FIG. 3 is a diagram showing a second blood flow measuring device included in the blood flow measurement system of FIG. 1.

FIGS. 4 and 5 are diagrams illustrating the operation of the blood flow measurement system of FIG. 1.

FIG. 6 is a diagram illustrating an embodiment of the blood flow measurement system of FIG. 1.

FIG. 7 is a diagram illustrating operation modes of the blood flow measurement system of FIG. 1.

FIGS. 8 and 9 are diagrams illustrating an operation example of the blood flow measurement system of FIG. 1.

BEST MODE

It should be noted that when reference numerals are given to components in the drawings in the specification, the same components are given the same number even if they are shown in different drawings.

Meanwhile, the meanings of the terms used herein should be understood as follows.

A singular form should be understood as including a plural form unless definitely defined in other ways in the contexts, and the right range should not be limited by these terms.

It should be understood that terms "comprise" or "have" do not exclude the possibility of existence or addition of one or more other features, numbers, steps, operations, components, parts, or a combination thereof.

Hereafter, preferred embodiments of the present disclosure deigned to solve the problems described above are described in detail with reference to the accompanying drawings.

FIG. 1 is a diagram showing a blood flow measurement system according to embodiments of the present disclosure, FIG. 2 is a diagram showing a first blood flow measuring device included in the blood flow measurement system of FIG. 1, FIG. 3 is a diagram showing a second blood flow measuring device included in the blood flow measurement system of FIG. 1, and FIGS. 4 and 5 are diagrams illustrating the operation of the blood flow measurement system of FIG. 1.

Referring to FIGS. 1 to 5, a blood flow measurement system according to an embodiment of the present disclosure may include a first blood flow measuring device 100 and a second blood flow measuring device 200. The first blood flow measuring device 100 may include a first image guide probe 110, and a 1_1 Doppler probe 120 and a 1_2 Doppler probe 130 disposed in a direction perpendicular to the first image guide probe 110. In an embodiment, the first blood flow measuring device 100 may include a first guide image probe 110, a 1_1 Doppler probe 120, and a 1_2 Doppler probe 130. The first guide image probe 110 includes a plurality of first image ultrasonic elements and may be disposed in a first direction D1. For example, the first direction D1 may show the left-right direction on the basis of FIG. 1 and the first image ultrasonic elements may include a 1_1 image ultrasonic element IE1_1, and a 1_2 image ultrasonic element IE1_2 to a 1_N image ultrasonic element IE1_N. The blood flow measurement system 10 according to the present disclosure can find out the position of a blood vessel by transmitting a first image ultrasonic transmission signal IUT1 to a target through the first guide image probe 110 and by implementing an ultrasonic image UI using a first image ultrasonic reception signal IUR1 reflected and received from the target. In this case, the target may be a portion of a human body.

The 1_1 Doppler probe 120 includes a plurality of 1_1 Doppler ultrasonic elements and may be disposed at a side of the first guide image probe 110 in a second direction D2 corresponding to a direction perpendicular to the first direction D1. For example, the 1_1 Doppler probe 120 may be disposed in the second direction D2 with respect to the first guide image probe 110, and the 1_1 Doppler ultrasonic elements may include a 1_1_1 Doppler ultrasonic element DE1_1_1, and a 1_1_2 Doppler ultrasonic element DE1_1_2 to a 1_1_K Doppler ultrasonic element DE1_1_K. In this case, K may be a natural number and K may be the same as or different from a natural number N. The blood flow measurement system 10 according to the present disclosure can output a spectrogram showing a 1_1 blood flow speed of a blood vessel in a target by transmitting a 1_1 Doppler ultrasonic transmission signal DUT1_1 through the 1_1 Doppler probe 120 and using a 1_1 Doppler ultrasonic reception signal DUR1_1 reflected and received from the target.

The 1_2 Doppler probe 130 includes a plurality of 1_2 Doppler ultrasonic elements and may be disposed at another side of the first guide image probe in a third direction D3 corresponding to a direction perpendicular to the first direction D1. For example, the 1_2 Doppler probe 130 may be disposed in the third direction D3 with respect to the first guide image probe 110, and the 1_2 Doppler ultrasonic elements may include a 1_2_1 Doppler ultrasonic element DE1_2_1, and a 1_2_2 Doppler ultrasonic element DE1_2_2 to a 1_2_K Doppler ultrasonic element DE1_2_K. The blood flow measurement system 10 according to the present disclosure can output a spectrogram showing a 1_2 blood flow speed of a blood vessel in a target by transmitting a 1_2 Doppler ultrasonic transmission signal DUT1_2 through the 1_2 Doppler probe 130 and using a 1_2 Doppler ultrasonic reception signal DUR1_2 reflected and received from the target.

The second blood flow measuring device 200 may include a second image guide probe 210, and a 2_1 Doppler probe 220 and a 2_2 Doppler probe 230 disposed in a direction perpendicular to the second image guide probe 210. In an embodiment, the second blood flow measuring device 200 may include a second guide image probe 210, a 2_1 Doppler probe 220, and a 2_2 Doppler probe 230. The second guide image probe 210 includes a plurality of second image ultrasonic elements and may be disposed in a first direction D1. For example, the second image ultrasonic elements may include a 2_1 image ultrasonic element IE2_1, and a 2_2 image ultrasonic element IE2_2 to a 2_N image ultrasonic element IE2_N. The blood flow measurement system 10 according to the present disclosure can find out the position of a blood vessel by transmitting a second image ultrasonic transmission signal IUT2 to a target through the second guide image probe 210 and by implementing an ultrasonic image UI using a second image ultrasonic reception signal IUR2 reflected and received from the target.

The 2_1 Doppler probe 220 includes a plurality of 2_1 Doppler ultrasonic elements and may be disposed at a side of the second guide image probe 210 in the second direction D2 corresponding to a direction perpendicular to the first direction D1. For example, the 2_1 Doppler probe 220 may be disposed in the second direction D2 with respect to the second guide image probe 210, and the 2_1 Doppler ultrasonic elements may include a 2_1_1 Doppler ultrasonic element DE2_1_1, and a 2_1_2 Doppler ultrasonic element DE2_1_2 to a 2_1_K Doppler ultrasonic element DE2_1_K.

The blood flow measurement system 10 according to the present disclosure can output a spectrogram showing a 2_1 blood flow speed of a blood vessel in a target by transmitting a 2_1 Doppler ultrasonic transmission signal DUT2_1 through the 2_1 Doppler probe 220 and using a 2_1 Doppler ultrasonic reception signal DUR2_1 reflected and received from the target.

The 2_2 Doppler probe 230 includes a plurality of 2_2 Doppler ultrasonic elements and may be disposed at another side of the second guide image probe 210 in the third direction D3 corresponding to a direction perpendicular to the first direction D1. For example, the 2_2 Doppler probe 230 may be disposed in the third direction D3 with respect to the second guide image probe 210, and the 2_2 Doppler ultrasonic elements may include a 2_2_1 Doppler ultrasonic element DE2_2_1, and a 2_2_2 Doppler ultrasonic element DE2_2_2 to a 2_2_K Doppler ultrasonic element DE2_2_K. The blood flow measurement system 10 according to the present disclosure can output a spectrogram showing a 2_2 blood flow speed of a blood vessel in a target by transmitting a 2_2 Doppler ultrasonic transmission signal DUT2_2 through the 2_2 Doppler probe 230 and using a 2_2 Doppler ultrasonic reception signal DUR2_2 reflected and received from the target.

In an embodiment, the first blood flow measuring device 100 may be disposed in a first blood vessel region BR1 corresponding to a blood vessel disposed in a first measurement direction MD1 with respect to the heart HT in a human body, and the second blood flow measuring device 200 may be disposed in a second blood vessel region BR2 corresponding to a blood vessel disposed in a second measurement direction MD2 corresponding to the opposite direction of the first measurement direction MD1 with respect to the heart HT. For example, the first measurement direction MD1 may be a direction from the heart HT to the head and the second measurement direction MD2 may be a direction from the heart HT to the legs. The blood vessel disposed in the first measurement direction MD1 with respect to the heart HT may be a first blood vessel BH1 and, for example, the first blood vessel BH1 may be a carotid artery. Further, the blood vessel disposed in the second measurement direction MD2 with respect to the heart HT may be a second blood vessel BH2 and, for example, the second blood vessel BH2 may be the aorta.

Further, a region having a preset predetermined gap from the first blood vessel BH1 along the first blood vessel BH1 may be a first blood vessel region BR1, and a region having a preset predetermined gap from the second blood vessel BH2 along the second blood vessel BH2 may be a second blood vessel region BR2. In this case, the first blood flow measuring device 100 may be disposed in the first blood vessel region BR1 and the second blood flow measuring device 200 may be disposed in the second blood vessel region BR2.

In an embodiment, the blood flow measurement system 10 may further include a ratio provider 300. The ratio provider 300 can provide a blood flow ratio FR corresponding to the ratio between the value of first blood flow information FI1 measured from the first blood flow measuring device 100 and the value of second blood flow information FI2 measured from the second blood flow measuring device 200. For example, the first blood flow information FI1 and the second blood flow information FI2 may include a velocity time interval (VTI), a stroke volume (SV), and cardiac output. The stroke volume (SV) and the cardiac output can be expressed as in the following [Equation 1] and [Equation 2].

$$SV = VTI * CSA \quad \text{[Equation 1]}$$

where SV may be a stroke volume, VTI may be a velocity time interval, and CSA may be the cross-sectional area of a blood vessel.

$$CO = VTI * CSA * HR \quad \text{[Equation 2]}$$

where CO may be cardiac output, VTI may be a velocity time interval, CSA may be the cross-sectional area of a blood vessel, and HR may be a heart rate.

For example, blood flow information FI may be cardiac output, the value of the cardiac output that is measured from the first blood flow measuring device 100 disposed in the first blood vessel region BR1 may be 3, and the value of the cardiac output that is measured from the second blood flow measuring device 200 disposed in the second blood vessel region BR2 may be 7. In this case, the blood flow ratio FR may be 3:7, and when the blood flow ratio FR is 3:7, the condition of a patient may be a normal state.

Further, the ratio provider included in the blood flow measurement system can provide a first total value corresponding to the sum of the value of the first blood flow information and the value of the second blood flow information. Further, the ratio provider can also provide a second total value corresponding to the sum of a first weight information value corresponding to the product of a first weight value and the value of the first blood flow information and a second weight information value corresponding to the product of a second weight value and the value of the second blood flow information. In this case, the second weight value may be a value obtained by subtracting the first weight value from 1.

The blood flow measurement system 10 according to the present disclosure can more effectively monitor the condition of a patent by measuring blood flow information at a plurality of points using a plurality of blood flow measuring devices including an image guide probe and a plurality of Doppler probes disposed in a direction perpendicular to the image guide probe.

FIG. 6 is a diagram illustrating an embodiment of the blood flow measurement system of FIG. 1, FIG. 7 is a diagram illustrating operation modes of the blood flow measurement system of FIG. 1, and FIGS. 8 and 9 are diagrams illustrating an operation example of the blood flow measurement system of FIG. 1.

Referring to FIGS. 1 to 9, the blood flow measurement system 10 may further include a result provider 400. The result provider 400 can provide a warning signal when a blood flow ratio FR departs from a predetermined reference range. For example, the blood flow ratio FR in a normal state may be 3:7. Thereafter, the value of the cardiac output that is measured from the first blood flow measuring device 100 disposed in the first blood vessel region BR1 may be 6, and the value of the cardiac output that is measured from the second blood flow measuring device 200 disposed in the second blood vessel region BR2 may be 4. In this case, the blood flow ration FR may be 6:4. In this case, when a blood flow ratio FR is abnormally measured out of 3:7 that is the blood flow ratio FR corresponding to the normal reference range of patients, the result provider 400 can inform the user of the blood flow measurement system 10 according to the present disclosure of an emergency situation by providing a warning signal of result signals RS.

In an embodiment, the blood flow measurement system 10 may further include a controller 900. The controller 900 can provide control signals CS for controlling the first blood flow measuring device 100 and the second blood flow measuring device 200. The blood flow measurement system 10 may include a plurality of operation modes MD. For example, the plurality of operation modes MD may include a first operation mode MD1 and a second operation mode MD2. The first operation mode MD1 may be an operation mode that drives the first image guide probe 110 and the second image guide probe 210 to find out a blood vessel disposed in a human body. Further, the second operation mode MD2 may be an operation mode that drives the 1_1 Doppler probe 120, the 1_2 Doppler probe 130, the 2_1 Doppler probe 220, and the 2_2 Doppler probe 230 to measure the blood flow information FI of a blood vessel after finding out the blood vessel using the first image guide probe 110 and the second image guide probe 210.

In the first operation mode MD1 of the plurality of operation modes, the controller 900 can drive the first guide image probe 110 and the second guide image probe 210 on the basis of a first control signal of the control signals, and a measuring unit 500 can measure the position information PI of a blood vessel on the basis of a first image ultrasonic reception signal IUR1 and a second image ultrasonic reception signal IUR2 that are received to the first guide image probe 110 and the second guide image probe 210.

In an embodiment, in the second operation mode MD2 of the plurality of operation modes after the first operation mode MD1, the controller 900 can alternately drive the 1_1 Doppler probe 120 and the 1_2 Doppler probe 130 at every driving interval corresponding to a preset predetermined time interval. For example, a plurality of time intervals may include a first time interval and a second time interval. During the first time interval, the controller 900 can transmit 1_1 Doppler ultrasonic transmission signal DUT1_1 to a blood vessel using the 1_1 Doppler probe 120 and can receive a 1_1 Doppler ultrasonic reception signal DUR1_1 reflecting from the blood vessel for the first time interval through the 1_1 Doppler probe 120. Thereafter, during the second time interval, the controller 900 can transmit 1_2 Doppler ultrasonic transmission signal DUT1_2 to the blood vessel using the 1_2 Doppler probe 130 and can receive a 1_2 Doppler ultrasonic reception signal DUR1_2 reflecting from the blood vessel for the second time interval through the 1_1 Doppler probe 120. This way can be also equally applied to the 2_1 Doppler probe 220 and the 2_2 Doppler probe 230.

In an embodiment, a 1_1 Doppler ultrasonic reception signal DUR1_1 reflecting from a blood vessel of a human body that is obtained from a 1_1 Doppler ultrasonic transmission signal DUT1_1 provided from the 1_1 Doppler probe 120 may be received to the 1_2 Doppler probe 130. For example, a plurality of time intervals may include a first time interval and a second time interval. During the first time interval, the controller 900 can transmit 1_1 Doppler ultrasonic transmission signal DUT1_1 to a blood vessel using the 1_1 Doppler probe 120 and can receive a 1_1 Doppler ultrasonic reception signal DUR1_1 reflecting from the blood vessel for the first time interval through the 1_2 Doppler probe 130. Thereafter, during the second time interval, the controller 900 can transmit 1_2 Doppler ultrasonic transmission signal DUT1_2 to the blood vessel using the 1_2 Doppler probe 130 and can receive a 1_2 Doppler ultrasonic reception signal DUR1_2 reflecting from the blood vessel for the second time interval through the 1_2 Doppler probe 130. This way can be also equally applied to the 2_1 Doppler probe 220 and the 2_2 Doppler probe 230.

The blood flow measurement system 10 according to the present disclosure can more effectively monitor the condition of a patent by measuring blood flow information at a plurality of points using a plurality of blood flow measuring devices including an image guide probe and a plurality of Doppler probes disposed in a direction perpendicular to the image guide probe.

The invention claimed is:

1. A blood flow measurement system comprising:

a first blood flow measuring device including a first image guide probe, and a first Doppler probe and a second Doppler probe that are disposed in a direction perpendicular to the first image guide probe; and a second blood flow measuring device including a second image guide probe, and a third Doppler probe and a fourth Doppler probe that are disposed in a direction perpendicular to the second image guide probe, wherein the first blood flow measuring device is configured to be disposed in a first blood vessel region corresponding to a blood vessel disposed in a first measurement direction with respect to a heart in a human body, and wherein the second blood flow measuring device is configured to be disposed in a second blood vessel region corresponding to a blood vessel disposed in a second measurement direction corresponding to the opposite direction of the first measurement direction with respect to the heart.

2. The blood flow measurement system of claim 1, further comprising:

at least one processor configured to provide a blood flow ratio corresponding to a ratio between a value of first blood flow information measured from the first blood flow measuring device and a value of second blood flow information measured from the second blood flow measuring device.

3. The blood flow measurement system of claim 2, wherein the at least one processor is further configured to provide a warning signal when the blood flow ratio departs from a predetermined reference range.

4. The blood flow measurement system of claim 3, wherein the first blood flow information and the second blood flow information include a velocity time interval (VTI), a stroke volume (SV), and cardiac output.

5. The blood flow measurement system of claim 4, wherein:

the first guide image probe including a plurality of first image ultrasonic elements and disposed in a first direction;

the first Doppler probe includes a plurality of first Doppler ultrasonic elements and disposed at a side of the first guide image probe in a second direction corresponding to a direction perpendicular to the first direction; and the second Doppler probe includes a plurality of second Doppler ultrasonic elements and disposed at another side of the first guide image probe in a third direction corresponding to a direction perpendicular to the first direction.

6. The blood flow measurement system of claim 5, wherein:

the second guide image probe includes a plurality of second image ultrasonic elements and disposed in the first direction;

the third Doppler probe includes a plurality of third Doppler ultrasonic elements and disposed at a side of the second guide image probe in the second direction corresponding to a direction perpendicular to the first direction; and the fourth Doppler probe includes a plurality of fourth Doppler ultrasonic elements and disposed at another side of the second guide image probe in the third direction corresponding to a direction perpendicular to the first direction.

7. The blood flow measurement system of claim 6, further comprising:

a controller configured to provide control signals for controlling the first blood flow measuring device and the second blood flow measuring device, wherein the blood flow measurement system includes a plurality of operation modes, and in a first operation mode of the plurality of operation modes, the controller drives the first guide image probe and the second guide image probe on the basis of a first control signal of the control signals, and a measuring unit measures position information of a blood vessel on the basis of a first image ultrasonic reception signal and a second image ultrasonic reception signal that are received to the first guide image probe and the second guide image probe.

8. The blood flow measurement system of claim 7, wherein in a second operation mode of the plurality of operation modes after the first operation mode, the controller alternately drives the first Doppler probe and the second Doppler probe at every driving interval corresponding to a preset predetermined time interval.

9. The blood flow measurement system of claim 8, wherein the second Doppler probe is configured to receive a Doppler ultrasonic reception signal reflecting from the blood vessel that is obtained from a Doppler ultrasonic transmission signal provided from the first Doppler probe.

10. The blood flow measurement system of claim 2, wherein blood flow measurement system provides a sum of the value of first blood flow information and the value of second blood flow information or a sum of a product of a first weight value and the value of first blood flow information and a product of a second weight value and the value of second blood flow information.

* * * * *